United States Patent
Basude et al.

(10) Patent No.: US 6,514,209 B1
(45) Date of Patent: Feb. 4, 2003

(54) METHOD OF ENHANCING ULTRASONIC TECHNIQUES VIA MEASUREMENT OF ULTRAHARMONIC SIGNALS

(75) Inventors: Raghuveer Basude, Philadelphia, PA (US); Margaret A. Wheatley, Media, PA (US)

(73) Assignee: Drexel University, Philadelphia, PA (US)

( * ) Notice: Subject to any disclaimer, the term of this patent is extended or adjusted under 35 U.S.C. 154(b) by 58 days.

(21) Appl. No.: 09/589,570

(22) Filed: Jun. 7, 2000

Related U.S. Application Data

(60) Provisional application No. 60/137,926, filed on Jun. 7, 1999.

(51) Int. Cl.⁷ .................................................. A61B 8/14
(52) U.S. Cl. ...................................................... 600/458
(58) Field of Search ............................... 600/437, 438, 600/443–447, 449, 453–458; 73/861.25; 424/9.5, 9.51, 9.52

(56) References Cited

U.S. PATENT DOCUMENTS

| | | | |
|---|---|---|---|
| 5,352,436 A | 10/1994 | Wheatley et al. ............... 424/9 |
| 5,567,415 A | 10/1996 | Porter ........................ 424/9.52 |
| 5,614,169 A | 3/1997 | Klaveness et al. .......... 424/9.52 |
| 5,637,289 A | 6/1997 | Klaveness et al. ............ 424/9.3 |
| 5,648,062 A | 7/1997 | Klaveness et al. .......... 424/9.34 |
| 5,678,553 A | * 10/1997 | Uhlendorf et al. ........... 600/458 |
| 5,686,060 A | 11/1997 | Schneider et al. .......... 424/9.52 |
| 5,695,740 A | 12/1997 | Porter ........................ 424/9.52 |
| 5,701,899 A | 12/1997 | Porter ................... 428/662.02 |
| 5,827,502 A | 10/1998 | Klaveness et al. .......... 424/9.52 |
| 2001/0021808 A1 | * 9/2001 | Shi et al. ..................... 600/438 |

FOREIGN PATENT DOCUMENTS

| | | |
|---|---|---|
| WO | WO 94/21301 | 9/1994 |
| WO | WO 97/29783 | 8/1997 |
| WO | WO 98/47540 | 10/1998 |

OTHER PUBLICATIONS de Jong et al., "Higher harmonics of vibrating gas–filled microspheres. Part one: simulations", *Ultrasonics 1994*; 32(6) :447–453.

Leighton, T.G.; "The Acoustic Bubble", *Academic Press*, San Diego, 1994; 413–424.

\* cited by examiner

*Primary Examiner*—Marvin M. Lateef
*Assistant Examiner*—Ali M. Imam
(74) *Attorney, Agent, or Firm*—Licata & Tyrrell P.C.

(57) ABSTRACT

Methods and apparatus for enhancing the capabilities of ultrasonic techniques through use of ultraharmonics are provided.

16 Claims, No Drawings

METHOD OF ENHANCING ULTRASONIC TECHNIQUES VIA MEASUREMENT OF ULTRAHARMONIC SIGNALS

This application claims the benefit of U.S. provisional application Serial No. 60/137,926, filed Jun. 7, 1999.

This invention was supported in part by funds from the U.S. government (NIH Grant No. HL 52901 and CA 52823) and the U.S. government may therefore have certain rights in the invention.

BACKGROUND OF THE INVENTION

Conventional diagnostic ultrasound techniques such as B-mode imaging are usually based on processing ultrasonic waves at their fundamental frequency ($f_0$). Using these ultrasound techniques, one can non-invasively and safely generate real-time images and Doppler data. However, the received signals are at times weak in contrast.

Until recently, ultrasonography lacked substances to be administered to patients to improve or increase the diagnostic yield. However, some contrast agents, most of which consist of gas microbubbles, have been introduced for use in ultrasound imaging. Gas microbubbles act as echo-enhancers by a similar mechanism to that for determining echoscattering in other cases of diagnostic ultrasound. Specifically, the backscattering echo intensity is proportional to the change in acoustic impedance between the blood and the gas making the bubbles. The difference in acoustic impedance at this interface is very high. In fact, all of the incident sound is reflected. However, the acoustic wave reflection is still insufficient to determine a strong enhancement since the microbubbles are very small and sparse within the circulation. Further, reflectivity is proportional to the fourth power of a particle's diameter and directly proportional to the concentration of the particles themselves (Calliada et al. *Eur. J. Radiol.* 1998 27(2):S157–60).

Microbubbles reached by an ultrasound signal resonate with a specific resonance frequency depending on the microbubble diameter. However, the fundamental resonance frequency is not the only frequency the bubble radiates. Multiple frequencies of the fundamental one are also emitted. These harmonic frequencies have decreasing intensity. However, the second frequency, known as the second harmonic, has been extensively used for diagnostic purposes. For example, it has been demonstrated that at very low pressures of approximately 20 kPa, there is a 17.5 to 26 dB enhancement in the second harmonic signals from ALBUNEX™, a contrast agent consisting of microspheres of human serum albumin suspended in a 5% solution of the same developed by Molecular Biosystems, San Diego, Calif. USA (Schrope, A. B., Newhouse, L. V. *Ultrasound Med. Biol.* 1993 9(7):567–579). Second harmonic imaging also permits imaging of extremely small vessels which can be missed with conventional methods (Calliada et al. *Eur. J. Radiol.* 1998 27(2):S157–60). Accordingly, second harmonics have been suggested as a route to exploit the diagnostic benefits of contrast imaging (Burns et al. *Radiology* 1992 182(P):142; Goldberg, B. B. *Ultrasound Contrast Agents* Martin Dunitz Ltd, London, 1997; de Jong et al. *Ultrasonics* 1994 32(6):447–453).

Apart from emitting widely known $2^{nd}$ harmonics and other higher harmonics, bubbles also emit subharmonics and ultraharmonics. Subharmonic detection of resonating microbubbles has been described (Lotsberg et al. 1996 99(3):1366–1369; Leighton, T. G.; The Acoustic Bubble Academic press, San Diego, 1994, p 413–424; Forsberg, F. and Shi, T. W. New Aspects of Harmonic and Subharmonic Imaging. Proc. Symp. The Leading Edge in Diagnostic Ultrasound. Atlantic City, p 24–27, May 19, 1998).

It has now been found that ultraharmonics can be effectively measured in objects subjected to ultrasonic techniques and that measurement of ultraharmonics enhances the capabilities of these techniques. For example, it has now been demonstrated that measurement of ultraharmonics of ultrasound contrast agents in ultrasonic techniques enhances the capabilities of ultrasonic contrast based techniques.

SUMMARY OF THE INVENTION

An object of the present invention is to provide a method of enhancing the capabilities of ultrasonic techniques which comprises subjecting an object to an ultrasonic technique; and measuring the ultraharmonic resonance in the object. In a preferred embodiment, the object comprises an ultrasound contrast agent capable of producing the ultraharmonic resonance. Alternatively, the object may comprise free microbubbles, echogenic scatteres or reflectors capable of producing the ultraharmonic resonance, or cells, tissues or a whole body.

Another object of the present invention is to provide ultrasound instruments and systems which measure ultraharmonics to enhance the capabilities of ultrasonic techniques.

DETAILED DESCRIPTION OF THE INVENTION

In addition to the fundamental frequency ($f_0$) generated by ultrasonic techniques, objects when subjected to ultrasonic techniques also generate subharmonic, harmonic and even ultraharmonic ($3/2f_0$, $5/2f_0$, etc.) frequencies. Unlike the fundamental frequency and harmonics which can also be generated due to non-linearity of the medium (i.e. surrounding tissue or water), ultraharmonics and subharmonics are characteristic of the object only.

Second harmonic enhancement in objects such as ultrasound contrast agents subjected to an ultrasonic technique is usually below 20 dB and decreases dramatically with increases in diagnostic pressure.

On the other hand, it has now been found that ultraharmonic enhancement of an object subjected to an ultrasonic technique is typically greater than 20 dB and usually increases with increase in diagnostic pressure. Accordingly, the present invention relates to methods and apparatus which measure ultraharmonic signals thereby enhancing the capabilities of ultrasonic techniques including, but not limited to, imaging, Doppler and perfusion techniques. These methods and apparatus are useful in both medical diagnostics and industrial applications.

As demonstrated herein measurement of ultraharmonic signals can be used to obtain higher contrast and signal to noise ratio with respect to tissue or water. In addition, measurement of ultraharmonic signals can be used to obtain higher Doppler resolution as compared to measurement of fundamental frequency. Moreover, since the first ultraharmonic is midway between the fundamental and second harmonic frequency, it is less attenuated than the second harmonics. Thus, ultraharmonics may be used to replace or augment the existing second harmonic techniques, to further harness the benefits of contrast only imaging, and other contrast based harmonic techniques, as described previously for second harmonic contrast based techniques.

Thus, by "enhancing the capabilities" of ultrasonic techniques, it is meant that higher contrast and signal to noise ratio with respect to tissue or water is achieved through measurement of ultraharmonic signals, along with higher Doppler resolution with respect to fundamental imaging techniques and decreased attenuation with respect to harmonics such as second harmonics.

In the method of the present invention, an object is subjected to an ultrasonic technique such as an imaging, Doppler or perfusion technique and the ultraharmonic signal of the object is measured. Examples of objects used in these methods include, but are not limited to, ultrasound contrast agents, free microbubbles, echogenic scatteres and reflectors, cells, tissues and whole bodies.

A series of experiments were performed to demonstrate enhanced capabilities of ultrasonics techniques wherein ultraharmonics were measured. In these experiments, a thin and flexible walled, surfactant based ultrasound contrast agent developed by insonating Span60 and Tween 80 as described in U.S. Pat. No. 5,352,436 was used as the object. Decafluorobutane or octafluoropropane gas was entrapped within the microbubbles of this thin and flexible walled, surfactant based contrast agent to produce ST68-PFC. Experiments were then performed to determine the frequency response of ST68-PFC.

The frequency content of the transmitted ultrasound signal in de-ionized (~18 M) water, 2"(50 mm) from the transducer was recorded as base. An increase in second harmonic and third harmonic generations was observed in deionized water due to non-linear propagation on increasing insonating pressure. Moreover, the generation of higher harmonics due to propagation in tissue is aggravated, since the non-linearity parameter B/A for tissue at diagnostic frequencies varies between 10 and 15. In pure water, B/A has been reported to equal 5 (de Jong et al. Ultrasonics. 1994 32(6):457–459). An agent such as ST68-PFC, which presents high backscattered enhancement over a broad range of frequencies (Forsberg et al. *Ultrasound Med. and Biol.* 1997 23(8) :1201–1208; and Forsberg et al. *IEEE* 1996 Ultrasonics Symposium 1337–1340), merely scatters this transformed insonating signal. This can be falsely attributed as agent generated second harmonics. In subsequent experiments at 1.29 MPa, it was observed that the agent generated second harmonic enhancement is practically nonexistent compared to the $2^{nd}$ harmonics generated due to non-linear propagation. No sub or ultraharmonics were observed in these experiments.

A comparison of the base frequency content to the frequency content with agent at an insonating positive peak-pressure of 38.2 kPa and 1.29 MPa was made. The first subharmonics ($f_0/2$), second and third harmonics ($2f_0$, $3f_0$), and first, second and third sub-harmonics ($3/2f_0$, $5/2f_0$, $7/2f_0$) in the signal from the agent could be clearly seen. However, the base signal only showed higher (second and third) harmonics. These data were primarily used for the purpose of comparing the ratio of the agent-generated harmonic signals to that of the base, using the same transducers in identical conditions. Thus, correction for the transducer bandwidth characteristics was not necessary. The signal obtained from the agent using a broad-band needle hydrophone at the a positive peak insonating pressure of 1.29 MPa was also determined.

It was found that ultraharmonic enhancement was typically greater than 20 dB (18 dB at 40 kPa for ST68-PFC), and usually increased with increase in pressure (approximately 35 dB at 0.5 MPa and 41 dB at 1.1 MPa for ST68-PFC). However, second harmonic enhancements were usually below 20 dB (typically 15 dB at 40 kPa for ST68-PFC), and decreased dramatically with increased pressure (approximately 5 dB at 0.5 MPa and 1 dB at 1.1 MPa). The first ultraharmonic ($3/2f_0$=7.5 MHZ) signal increased with increase in dose, while the first sub-harmonic ($1/2f_0$=2.5 MHZ) signal decreased.

Thus, in the method of the present invention capabilities of non-medical ultrasonic techniques including, but not limited to, imaging, Doppler, and perfusion techniques involving the detection of objects such as free microbubbles, contrast agents, scatteres or reflectors, or whole bodies such as fish, are enhanced by subjecting the object to the ultrasonic technique and measuring the ultraharmonic resonance of the object subjected to the ultrasonic technique.

The method of the present invention is also useful in ultrasonic techniques used in medical diagnosis. In this embodiment, it is preferred that the object comprise an ultrasound contrast agent which is administered to a patient, cells or tissue. Multiple ultrasonic contrast agents for administration to patients have been described in the prior art. For example, WO 9847540 discloses contrast agents for diagnostic ultrasound and targeted disease imaging and drug delivery comprising a dispersion of a biocompatible azeotropic mixture which contains a halocarbon; WO 9729783 discloses a contrast agent which comprises an aqueous dispersion of gas microbubbles stabilized by amphiphilic material containing phospholipid molecules having an overall net charge; U.S. Pat. No. 5,695,740, U.S. Pat. No. 5,567,415 and U.S. Pat. No. 5,701,899 disclose a pharmaceutically acceptable ultrasound contrast agent comprising microbubbles with an internal atmosphere enhanced with a perfluorocarbon gas; WO 9421301 discloses an ultrasound agent consisting of a biocompatible oil-in-water emulsion in which the oil phase comprises an oil-soluble gas/fluid or gas precursor; U.S. Pat. No. 5,637,289, U.S. Pat. No. 5,648,062, U.S. Pat. No. 5,827,502; and U.S. Pat. No. 5,614,169 disclose contrast agents comprising water-soluble, microbubble generating carbohydrate microparticles, admixed with at least 20% of a non-surface active, less water-soluble material, a surfactant or an amphiphillic organic acid; U.S. Pat. No. 5,686,060 describes an injectable suspension for ultrasonic echography comprising a carrier liquid containing at least $10^7$ microbubbles per milliliter and at least one saturated phospholipid at a concentration below 0.01% by weight. In a preferred embodiment, ultrasonic contrast agents used in the method of the present invention comprise either free microbubbles or ST68-PFC.

Ultrasound contrast agents used in the present invention may further comprise drugs or targeting moieties encompassed within or attached to the contrast agents. Such agents are useful in drug delivery and targeting techniques. Ultrasound contrast agents comprising the drug can then be delivered to an imaged site by insonation of the agent, causing the matrix to vibrate and release drug. It is also possible that the insonation will cause the ultrasound contrast agent to rupture, releasing part or all of any contents trapped within the matrix or within the hollow interior of the agent. A targeting moiety such as an antibody specific for a selected tissue can also be attached to the ultrasound contrast agent for targeted delivery of the agent.

Also provided in the instant invention are ultrasonic instruments capable of measuring ultraharmonic signals generated by an object subjected to an ultrasonic technique. In simplest form, the ultrasound instrument that measures ultraharmonic signals comprises at least one transducer capable of transmitting an ultrasound at frequency ($f_0$) and receiving ultraharmonics of the transmitted frequency ($3f_0/2$). In one embodiment, the instrument comprises multiple transducers. For example, the instrument may comprise a combination of broad-band and narrow band array transducers capable of transmitting ultrasound at a selected frequency ($f_0$) and also receiving ultraharmonic signals of the transmitted frequency ($3f_0/2$). Thus, in this embodiment, the instrument could transmit ultrasound at a selected fundamental frequency of 5 MHZ and receive ultraharmonics of the transmitted fundamental frequency at 7.5 MHZ, thereby encompassing Doppler or any other frequency shift of the ultraharmonics. Alternatively, the instrument could transmit ultrasound at a selected fundamental frequency of 2 MHZ and receive ultraharmonics of the transmitted fundamental frequency at 3 MHZ, also encompassing Doppler or any other frequency shift of the ultra-harmonics. In a preferred embodiment, the transducer is also capable of measuring harmonic and subharmonic signals. The ultrasound instrument may further comprise a software filter connected to the transducer which processes received ultrasound signals at ultraharmonics($3f_0/2$) of the transmitted frequency($f_0$) or an analog or digital hardware filter which processes received ultrasound signals at ultraharmonics($3f_0/2$) of the transmitted frequency($f_0$).

In a preferred embodiment, the instrument comprises an ultrasonic diagnostic imaging system capable of imaging the ultraharmonic response of objects such as contrast agents, echogenic entities or tissues inside a body with reduced clutter. This system comprises a transmit controller operable to cause the elements of an array transducer to transmit wave components which are of insufficient energy to stimulate a significant harmonic response in the near field but which are focused to develop higher intensity energy at a greater depth. The system also comprises an array transducer responsive to the transmit controller for transmitting ultrasonic energy into the object at a fundamental frequency and for receiving ultrasonic echo signals at an ultraharmonic of the fundamental frequency. In one embodiment, the array transducer comprises a plurality of transducer elements for transmitting ultrasonic energy at a fundamental frequency and for receiving ultrasonic echo signals at an ultraharmonic of the fundamental frequency. In this embodiment, the transducer elements exhibit a response characteristic which encompasses both the fundamental frequency and the ultraharmonic of the fundamental frequency. A beamformer which processes echo signals from the transducer elements of this array transducer to form coherent echo signals is also used in the system along with a circuit for passing ultraharmonic frequency echo signals to the substantial exclusion of signals at the fundamental frequency and higher harmonics such as second harmonics. In one embodiment, the circuit for passing ultrasonic echo signals at an ultraharmonic of the fundamental frequency comprises a filter defining a passband which includes the ultraharmonic frequency to the substantial exclusion of the fundamental frequency and higher harmonics. This filter also substantially excludes multipath clutter at the fundamental frequency. For example, a programmable digital filter can be used. The system also comprises an image processor, responsive to ultraharmonic frequency echo signals passed by said circuit, for producing an ultrasonic ultraharmonic image. For example, a B mode processor which produces ultraharmonic images can be used. It is preferred that the B mode processor include an amplitude detector for detecting the envelope of the ultraharmonic echo signals.

Ultrasonic diagnostic imaging systems for imaging the ultraharmonic response of objects inside a body or any heterogeneous nonlinear medium which exhibit depth dependent attenuation of ultrasonic energy can also be developed. The system comprises a transmit controller operable to cause the elements of an array transducer to transmit wave components, the energy of which is distributed over the array in the near field and becomes focused to develop ultraharmonic frequency components at a focal depth. The system also comprises a transducer array responsive to the transmit controller for transmitting ultrasonic energy into the body or other medium at a fundamental frequency. In a preferred embodiment, the fundamental frequency is equal to or less than 6 MHZ. The transducer array also receives ultrasonic echo signals from the object at an ultraharmonic of the fundamental frequency, preferably equal to or less than 9 MHZ or 15 MHZ. In another embodiment, the transducer array transmits ultrasonic energy into the body at a fundamental frequency which is equal to or less than 3 MHZ and the transducer array receives ultrasonic echo signals at an ultraharmonic of the fundamental frequency which is equal to or less than 4.5 MHZ. In yet another embodiment, the transducer array transmits ultrasonic energy into the body at a fundamental frequency which is less than 2 MHZ and the transducer array receives ultrasonic echo signals from tissue at a harmonic of the fundamental frequency which is less than 3 MHZ. This system further comprises a means for digitizing the received ultrasonic echo signals; a digital beamformer for forming coherent echo signals from the digitized ultrasonic echo signals; a filter which passes ultraharmonic echo signals to the substantial exclusion of fundamental frequency signals and higher harmonics; and an image processor which is responsive to the ultraharmonic echo signals from which fundamental frequency signals have been substantially excluded and which produces an ultrasonic image from the ultraharmonic echo signals. In a preferred embodiment, the filter comprises a programmable digital filter which is programmed to pass a band of ultraharmonic echo signals to the substantial exclusion of signals of the fundamental frequency, including the substantial exclusion of multipath clutter at said fundamental frequency. Accordingly, this system also substantially reduces the multipath clutter of the image. This ultrasonic diagnostic imaging system of the present invention is particularly useful in ultrasonic techniques of tissue or cells of the body with or without any ultrasound contrast agents.

The systems of the present invention are useful in producing an ultrasonic image or Doppler signals from the ultraharmonic response of an object such as a tissue or contrast agent in the interior of the body or any medium. In this method, ultrasonic energy is transmitted from the elements of an array transducer into the body or medium at a fundamental frequency in wave components emanating over a plurality of elements in the near field. The wave components are focused to develop ultraharmonic frequency components at a greater death. Ultrasonic echo signals returned at an ultraharmonic of the fundamental frequency are also received by this array transducer and coherent echo signals from the received ultrasonic echo signals are formed. The steps of transmitting and receiving can be accomplished using an ultrasonic probe with a transducer array to transmit fundamental frequency ultrasonic energy and receive ultraharmonic echo signals from the object. An ultrasonic image of the signals which substantially excludes the fundamental frequency and harmonic signals is then produced and displayed. By measuring the ultrasonic signal via this system, multipath clutter in the image is substantially reduced.

The following nonlimiting examples are provided to further illustrate the present invention.

EXAMPLES

Example 1

Experimental Set-Up

A custom-built acrylic tank (30.5×26.7×25.4 cm) was filled with freshly degassed de-Ionized (~18 MΩ) water. An acrylic sample container (5×10×17.8 cm), having a 5×5 cm acoustic window was filled with 750 ml of phosphate buffered saline (PBS) (NaCl [8.01 grams], KCl [0.194 grams], Na$_2$HPO$_4$[0.909 grams], and KH$_2$PO$_4$[0.191 grams] in one liter of water) and placed inside the tank at approximately 30 mm from the back of the tank and 75 mm from the sides. The cover of the tank was fitted with a x-y positioning system (Edmund Scientific, Barrington, N.J., USA) to mount the ultrasonic transducers. The contents of the sample container were constantly stirred using a magnetic stirrer.

A HP 8116A function generator was used to generate a 5 MHZ sine wave with a 5 $\mu$sec burst, at a pulse repetition frequency of 10 Hz. This signal was amplified using an ENI A150 power amplifier and fed to the transmitting transducer. Two single element, broadband, 12.7 mm (0.5") element diameter, 50.8 mm (2") Point focussed transducers (Panametrics, Waltham, Mass.) with center frequencies of 5 MHZ and 10 MHZ, respectively, were used such that their beams crossed inside the sample container at their focus (50 mm). The −6 dB bandwidths of the transducers were 91.74% and 65.31% respectively. A known dose (example: 0.1 $\mu$l/1 ml of PBS) of ST68-PFC was injected into the container, and acoustic data were collected after a 10 second initial delay to ensure proper mixing. The received signals from the focus were pre-amplified using a Panametrics 5072PR pulser/receiver by 40 dB, and fed to the digitizing oscilloscope LeCroy 9350A. Base measurements were recorded in plain PBS buffer by placing an Air-interface reflector (15 $\mu$m plastic sheet backed with air) in the container, at the focus of the two transducers. The experiment was repeated at six different pressure levels between 38.2 kPa and 1.29 MPa, at 10 different doses from 30 $\mu$l to 200 $\mu$l in 750 ml of PBS buffer (0.04–0.26 $\mu$l/ml). The insonating pressure at the focus was measured using a 0.5 mm diameter needle hydrophone (Precision Acoustics, Dorset, UK.), and the doses of agent were delivered using Pipetman (Rainin, Mass. USA.) pipettes.

Digital Fast Fourier Transform (DFFT) was performed on the received signal to obtain a Power Spectrum, and an average of 50 such Power Spectra were used to depict the data at each pressure level. The harmonic content of the averaged Power Spectrum was determined relative to the fundamental frequency ($f_0$=5 MHZ), and the difference in the harmonic content with the agent present to that of the base (blank PBS) was reported as dB enhancement.

What is claimed is:

1. A method of enhancing the capabilities of ultrasonic techniques comprising:
   (a) subjecting an object comprising an ultrasound contrast agent capable of producing ultraharmonic resonance to an ultrasonic technique; and
   (b) measuring ultraharmonic signals of the object to the substantial exclusion of the fundamental frequency and higher harmonics.

2. The method of claim 1 wherein the object comprises free microbubbles.

3. The method of claim 1 wherein the object comprises echogenic scatteres or reflectors.

4. The method of claim 1 wherein the object comprises cells, tissue or a whole body.

5. The method of claim 1 wherein the ultrasonic technique comprises a Doppler, perfusion, or imaging technique.

6. The method of claim 1 further comprising measuring harmonic or subharmonic signals of the object.

7. An ultrasound instrument that measures ultraharmonic signals comprising a combination of broad band and narrow band array transducers capable of transmitting an ultrasound at frequency ($f_0$) and receiving ultraharmonics of the transmitted frequency ($3f_0/2$) to the substantial exclusion of the fundamental frequency and higher harmonics.

8. The ultrasound instrument of claim 7 further comprising a software filter connected to the transducer which processes received ultrasound signals at ultraharmonics($3f_0/2$) of the transmitted frequency($f_0$).

9. The ultrasound instrument of claim 7 further comprising an analog or digital hardware filter which processes received ultrasound signals at ultraharmonics($3f_0/2$) of the transmitted frequency($f_0$).

10. The ultrasound instrument of claim 7 further comprising a combination of hardware and software to process the received ultrasound signals at ultraharmonics($3f_0/2$) of the said transmitted frequency($f_0$).

11. An ultrasonic diagnostic imaging system for imaging the ultraharmonic response of an object with reduced clutter comprising:
   (a) a transmit controller operable to cause the elements of an array transducer to transmit wave components which are of insufficient energy to stimulate a significant harmonic response in the near field, but which are focused to develop higher intensity energy at a greater depth;
   (b) an array transducer responsive to said transmit controller for transmitting ultrasonic energy into the object at a fundamental frequency and responsive to the transmitted ultrasonic energy, said array transducer receiving ultrasonic echo signals at an ultraharmonic of the fundamental frequency wherein said array transducer for transmitting and for receiving comprises an ultrasonic transducer array probe which comprises a plurality of transducer elements for transmitting ultrasonic energy at a fundamental frequency and for receiving ultrasonic echo signals at an ultraharmonic of the fundamental frequency;
   (c) a beamformer which processes echo signals from the array transducer to form coherent echo signals:
   (d) a circuit for passing ultraharmonic frequency echo signals to the substantial exclusion of signals at the higher harmonics and at said fundamental frequency; and
   (e) an image processor responsive to ultraharmonic frequency echo signals passed by said circuit, for producing an ultrasonic ultraharmonic image whereby multipath clutter in said ultraharmonic image is substantially reduced.

12. An ultrasonic diagnostic imaging system for imaging the ultraharmonic response of tissue and contrast agents inside a body or any medium which exhibits depth dependent attenuation of ultrasonic energy comprising:
   (a) a transmit controller operable to cause the elements of an array transducer to transmit wave components, the energy of which is distributed over the array in the near field and becomes focused to develop ultraharmonic frequency components at a focal depth;
   (b) a transducer array responsive to said transmit controller for transmitting ultrasonic energy into the body or medium at a fundamental frequency which is equal to or less than 6 MHZ and which is responsive to the transmitted ultrasonic energy for receiving ultrasonic echo signals from the tissue or medium at an ultraharmonic of the fundamental frequency which is equal to or less than 9 MHZ or 15 MHZ;
   (c) a means for digitizing the received ultrasonic echo signals;

(d) a digital beamformer for forming coherent echo signals from the digitized ultrasonic echo signals;

(e) a filter which passes ultraharmonic echo signals to the substantial exclusion of fundamental frequency signals and higher harmonics frequency signals; and (f) an image processor responsive to the ultraharmonic echo signals from which fundamental frequency signals have been substantially excluded for producing an ultrasonic image from the ultraharmonic echo signals, whereby the multipath clutter of image is substantially reduced.

13. The ultrasonic diagnostic imaging system of claim 12, wherein said transducer array transmits ultrasonic energy into the body or medium at a fundamental frequency which is equal to or less than 3 MHZ and said transducer array receives ultrasonic echo signals at a harmonic of the fundamental frequency which is equal to or less than 4.5 MHZ.

14. The ultrasonic diagnostic imaging system of claim 12, wherein said transducer array transmits ultrasonic energy into the body or medium at a fundamental frequency which is less than 2 MHZ and said transducer array receives ultrasonic echo signals from tissue at a harmonic of said fundamental frequency which is less than 3 MHZ.

15. The ultrasonic diagnostic imaging system of claim 12, wherein said filter comprises a programmable digital filter which is programmed to pass a band of the ultraharmonic echo signals to the substantial exclusion of signals of the fundamental frequency including the substantial exclusion of multipath clutter at the fundamental frequency.

16. A method for producing an ultrasonic image or Doppler signals from an ultraharmonic response of an object in the interior of the body or any medium comprising the steps of:

(a) transmitting ultrasonic energy from the elements of an array transducer into a body or medium at a fundamental frequency in wave components emanating over a plurality of elements in the near field and which wave components become focused to develop ultraharmonic frequency components at a greater death;

(b) receiving ultrasonic echo signals by said array transducer which have been returned at an ultraharmonic of the fundamental frequency; (c) forming coherent echo signals from the received ultrasonic echo signals;

(d) passing ultraharmonic signals to the substantial exclusion of fundamental frequency signals and higher harmonic frequency signals;

(e) processing the ultraharmonic signals from which fundamental frequency and harmonic signals have been substantially excluded to produce ultrasonic image display signals; and (f) displaying the ultrasonic image display signals, whereby multipath clutter in said ultraharmonic ultrasonic image is substantially reduced.

* * * * *